(12) United States Patent
Hakkens

(10) Patent No.: US 10,485,400 B2
(45) Date of Patent: Nov. 26, 2019

(54) TUBE AND STEERABLE INTRODUCTION ELEMENT COMPRISING THE TUBE

(71) Applicant: KONINKLIJKE PHILIPS N.V., Eindhoven (NL)

(72) Inventor: Franciscus Johannes Gerardus Hakkens, Eersel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 14/425,931

(22) PCT Filed: Sep. 27, 2013

(86) PCT No.: PCT/IB2013/058908
§ 371 (c)(1),
(2) Date: Mar. 4, 2015

(87) PCT Pub. No.: WO2014/049555
PCT Pub. Date: Apr. 3, 2014

(65) Prior Publication Data
US 2015/0282693 A1    Oct. 8, 2015

Related U.S. Application Data

(60) Provisional application No. 61/706,850, filed on Sep. 28, 2012.

(51) Int. Cl.
*A61B 1/00* (2006.01)
*A61L 29/14* (2006.01)
(Continued)

(52) U.S. Cl.
CPC ........ *A61B 1/00071* (2013.01); *A61B 1/0011* (2013.01); *A61B 1/00078* (2013.01);
(Continued)

(58) Field of Classification Search
CPC . A61F 2/06; A61M 25/0141; A61M 25/0158; A61M 25/0133–0158
See application file for complete search history.

(56) References Cited

U.S. PATENT DOCUMENTS 4,149,911 A * 4/1979 Clabburn ................ C22F 1/006
148/402
4,427,000 A * 1/1984 Ueda .................... A61B 1/0058
219/201

(Continued)

FOREIGN PATENT DOCUMENTS

JP   S592344 A    3/1980
JP   S63258681 A  10/1988
(Continued)

OTHER PUBLICATIONS

Leng, J. et al. "Shape memory polymers and their composites: Stimulus methods and applications". Progress in Materials Science 56, pp. 1077 to 1135 (2011).

*Primary Examiner* — Jason E Flick
*Assistant Examiner* — John A Doubrava

(57) ABSTRACT

A tube for a steerable introduction element like a catheter, an endoscope or a sheath includes composite material of a shape memory alloy material and a non-shape-memory polymer material. The tube is used for making the introduction element steerable in a relatively easy way by modifying the temperature of the tube as required for achieving a preferred bending of the introduction element.

10 Claims, 5 Drawing Sheets

(51) Int. Cl.
*A61M 25/01* (2006.01)
*A61L 29/12* (2006.01)
*A61M 25/00* (2006.01)

(52) U.S. Cl.
CPC ............ *A61L 29/126* (2013.01); *A61L 29/14* (2013.01); *A61M 25/0009* (2013.01); *A61M 25/0102* (2013.01); *A61M 25/0158* (2013.01); *A61L 2400/16* (2013.01)

(56) References Cited

U.S. PATENT DOCUMENTS

| | | | | |
|---|---|---|---|---|
| 4,543,090 | A * | 9/1985 | McCoy | A61M 25/0158 600/151 |
| 4,601,283 | A * | 7/1986 | Chikama | A61B 1/31 219/201 |
| 4,930,494 | A * | 6/1990 | Takehana | A61B 1/00147 600/145 |
| 5,069,226 | A * | 12/1991 | Yamauchi | A61L 31/022 600/434 |
| 5,188,111 | A * | 2/1993 | Yates | A61B 1/0058 128/DIG. 7 |
| 5,231,989 | A * | 8/1993 | Middleman | A61B 1/00165 600/434 |
| 5,405,337 | A * | 4/1995 | Maynard | A61M 25/0158 604/531 |
| 5,662,621 | A | 9/1997 | Lafontaine | |
| 6,072,154 | A * | 6/2000 | Maynard | A61B 1/0058 219/209 |
| 6,264,684 | B1 * | 7/2001 | Banas | A61F 2/86 606/195 |
| 6,575,965 | B1 * | 6/2003 | Fitch | A61B 17/12022 606/15 |
| 6,585,717 | B1 * | 7/2003 | Wittenberger | A61M 25/0138 604/523 |
| 6,758,858 | B2 * | 7/2004 | McCrea | A61F 2/06 623/1.13 |
| 6,872,433 | B2 * | 3/2005 | Seward | A61L 29/126 428/35.7 |
| 8,034,046 | B2 * | 10/2011 | Eidenschink | A61L 29/04 604/264 |
| 9,889,273 | B2 * | 2/2018 | Cully | A61M 25/0102 |
| 9,918,772 | B2 * | 3/2018 | Fischer | A61B 18/02 |
| 2002/0002371 | A1 * | 1/2002 | Acker | A61B 17/2202 606/27 |
| 2002/0142119 | A1 * | 10/2002 | Seward | A61L 29/126 428/36.9 |
| 2003/0055479 | A1 * | 3/2003 | Jayaraman | A61F 2/88 623/1.1 |
| 2004/0193257 | A1 * | 9/2004 | Wu | A61F 2/90 623/1.46 |
| 2005/0038333 | A1 * | 2/2005 | Sra | A61B 18/1492 600/374 |
| 2011/0125188 | A1 | 5/2011 | Goraltchouk et al. | |
| 2012/0035592 | A1 | 2/2012 | Eidenschink | |
| 2014/0228831 | A1 * | 8/2014 | Fischer | A61B 18/02 606/21 |
| 2014/0276642 | A1 * | 9/2014 | Cully | A61M 25/0102 604/525 |
| 2015/0282693 | A1 | 10/2015 | Hakkens | |

FOREIGN PATENT DOCUMENTS

| | | |
|---|---|---|
| JP | 2003513746 A | 4/2003 |
| JP | 2010252615 A | 11/2010 |
| WO | 0135859 A1 | 5/2001 |

* cited by examiner

TUBE AND STEERABLE INTRODUCTION ELEMENT COMPRISING THE TUBE

CROSS-REFERENCE TO PRIOR APPLICATIONS

This application is the U.S. National Phase application under 35 U.S.C. § 371 of International Application Serial No. PCT/IB2013/058908, filed on Sep. 27, 2013, which claims the benefit of U.S. Application Ser. No. 61/706,850, filed on Sep. 28, 2012. These applications are hereby incorporated by reference herein.

FIELD OF THE INVENTION

The invention relates to a tube and a steerable introduction element like a catheter, an endoscope or a sheath comprising the tube. The invention relates further to a production method and a production apparatus for producing the tube.

BACKGROUND OF THE INVENTION

U.S. Pat. No. 6,872,433 B2 discloses an apparatus for minimally invasive applications. The apparatus has a longitudinal axis with the apparatus extending in a radial direction from the longitudinal axis and wherein the apparatus is activated by a change in temperature. The apparatus comprises a first unit with a first structure for at least positioning the apparatus, wherein the first structure includes a quantity of shape memory alloy. The apparatus further comprises a second unit with a second structure for at least positioning the apparatus, wherein the second structure includes a quantity of shape memory polymer. The first unit has a longitudinally extending coiled configuration with more than one wrap and the second unit comprises a cylinder, wherein the first unit is positioned in the second unit such that changes in temperature of the shape memory alloy cause the first unit to change position by a radial contraction and a longitudinal extension and to stretch the second unit comprising the second structure including the shape memory polymer along the longitudinal axis.

SUMMARY OF THE INVENTION

The combination of a shape memory alloy and a shape memory polymer is not very stable. Moreover, the shape memory polymer changes its properties, when being heated. This leads to a reduced accuracy of positioning the apparatus.

It is an object of the present invention to provide a tube and a steerable introduction element comprising the tube, which allow for an increased accuracy of positioning the steerable introduction element. It is a further object of the present invention to provide a production apparatus and a production method for producing the tube.

In a first aspect of the present invention a tube comprising a composite material including a shape memory alloy material and a non-shape-memory polymer material is presented.

The tube material can be used to make an introduction element like a catheter, endoscope or sheath, which comprises the tube, steerable in a relatively easy way by modifying the temperature of the tube as required for achieving a preferred bending of the introduction element. Moreover, by using this steering mechanism the introduction element can be positioned relatively accurately, because the composite material includes a non-shape-memory polymer material, which is more stable than a shape-memory polymer material and which may be optimized for other properties like hardness, stiffness, et cetera. Furthermore, since the composite material includes the non-shape-memory polymer material a wide range of potential materials, which have been proven for a wide range of applications and characteristics, is available, which can be used, for instance, for adapting the tube to requirements of a desired application. Moreover, using the tube for steering an introduction element can lead to cost reductions and can enable miniaturization.

The shape memory alloy material comprises preferentially elongated shape memory alloy elements like shape memory alloy fibers which may be shape memory alloy wire pieces. The elongated shape memory alloy elements can increase the stiffness of the tube.

The shape memory alloy material comprises preferentially nitinol. For instance, nitinol fibers may be used as the shape memory alloy material. Nitinol is biocompatible such that it allows using the tube in medical applications.

The adhesion between the elongated shape memory alloy elements and the non non-shape-memory polymer is preferentially good enough for allowing the non-shape-memory polymer to follow a change in length of the elongated shape memory alloy elements. For instance, if the elongated shape memory alloy elements shrink or become longer again, the good adhesion ensures that the non-shape-memory polymer material can follow these length changes. Moreover, the good adhesion can ensure that stress applied by the non-shape-memory polymer on the elongated shape memory alloy elements will reset them to the original size after stopping a thermal activation. For providing this good adhesion the surface of the elongated shape memory alloy elements can be surface treated. For instance, the elongated shape memory alloy elements can have a roughened surface. The surface of the shape memory alloy elements can be roughened by, for instance, grinding, rolling, forging, in particular, making indents, etching, blasting or any other roughening technique. Also other surface treatments can be used for improving the adhesion between the elongated shape memory alloy elements and the non-shape-memory polymer material like surface coatings.

The non-shape-memory polymer material is preferentially a conventional polymer like thermoplastic, silicone or thermoset. It may also comprise a combination of two or all of these exemplarily mentioned conventional polymers. The non-shape-memory polymer material is not a shape memory polymer material like the shape memory polymer material disclosed in, for instance, the article "Shape-memory polymers and their composites: Stimulus methods and applications" by J. Leng et al., Progress in Materials Science 56, pages 1077 to 1135 (2011).

The tube is preferentially producible by using a polymer shaping technique. The polymer shaping technique is preferentially a conventional one like extrusion or injection molding, i.e. the tube may be producible by extrusion and/or injection molding. In the extrusion process the shape memory alloy material, in particular, the elongated shape memory alloy elements, which may be chopped fibers or wire pieces, will align in the length direction of the tube automatically. If the shape memory alloy elements, especially the shape memory alloy fibers, align in the length direction of the tube, they are more effective in creating a bending response. For instance, less shape memory alloy material may be required for the same bending response.

It is preferred that the composite material comprises a further material for modifying at least one of the thermal conductivity, the electrical resistance and the stiffness of the tube. For instance, the further material may include conductive particles, in particular, thermally and/or electrically conductive particles. It may comprise a metal material and/or a carbon material like carbon nanotubes and/or a ceramic material. By mixing a further material into the composite material it is possible, for example, to make the composite material itself a heating element, wherein in this case the tube just needs to be electrically connected to be heated by resistive heating. The further material can also be used to optimize the response of the tube to a thermal stimulus by modifying the thermal conductivity of the composite material as desired.

In further aspect of the present invention a steerable introduction element for being introduced into an object is presented, wherein the steerable introduction element comprises:

a tube as defined in claim 1, and a temperature modifying element for modifying the temperature of at least a part of the tube for bending the tube.

By modifying the temperature of at least a part of the tube the temperature of the tube can be modified, i.e. heated or cooled, especially locally, causing the tube to bend. The steerable introduction element can therefore also be regarded as being a steerable tube.

The steerable introduction element is preferentially a steerable sheath, a steerable catheter or a steerable endoscope. The steerable sheath can be pulled over another instrument like a conventional catheter, in order to make the other instrument steerable. The tube can be combined with a further tube. For instance, the tube with the composite material including shape memory alloy material and non-shape-memory polymer material can be an intermediate tube arranged in between an outer tube and an inner tube.

The temperature modifying element preferentially comprises at least one of a heating element and a cooling element. The heating element is preferentially adapted to heat a wall of the tube at one side, in order to cause the tube to bend. The cooling element can be used to reset the steerable introduction element faster into its original position, after a thermal activation by heating has been stopped.

The heating element is preferentially adapted to heat the part of the tube by at least one of resistive heating, fluidic heating and optical heating. In particular, the heating element can be adapted to apply an electrical current to the tube such that the tube material itself can be resistively heated. Or, the heating element can comprise a separate element being adapted to heat the part of the tube by fluidic, especially liquid, or optical heating. For instance, the heating element can comprise an optical fiber or another optical means for providing light to be absorbed by the part of the tube to be heated.

The cooling element can be adapted to provide a fluidic cooling. In particular, the cooling element can be adapted to provide a liquid cooling for cooling a part of the tube for bending the same. Instead of providing an active cooling, the temperature modifying element may only comprise a heating element for heating the tube, wherein in this case natural cooling by, for instance, conduction of heat through elements of the introduction element may be used, for example, through metal parts of the introduction element such as a braiding or a coil.

In an embodiment the temperature modifying element comprises several temperature modifying sub elements located at different locations for modifying the temperature of different parts of the tube, wherein at least two of the temperature modifying sub elements are separately from each other controllable. By addressing different temperature modifying sub elements different bendings of the tube can be obtained for steering the introduction element as desired. For instance, the temperature modifying sub elements can be heating sub elements, wherein the multiple heating sub elements can be used for bending in different directions, in particular, in all directions, preferentially at any location of the tube length.

In another aspect of the present invention a production apparatus for producing a tube as defined in claim 1 is presented, wherein the production apparatus comprises:

a composite material providing unit for providing a composite material comprising shape memory alloy material and non-shape-memory polymer material, a polymer shaping unit for producing the tube by applying a polymer shaping technique to the composite material.

In a further aspect of the present invention a production method for producing a tube as defined in claim 1 is presented, wherein the production method comprises:

providing a composite material comprising shape memory alloy material and non-shape-memory polymer material, producing the tube by applying a polymer shaping technique to the composite material.

It shall be understood that the tube of claim 1, the steerable introduction element of claim 9, the production apparatus of claim 14 and the production method of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
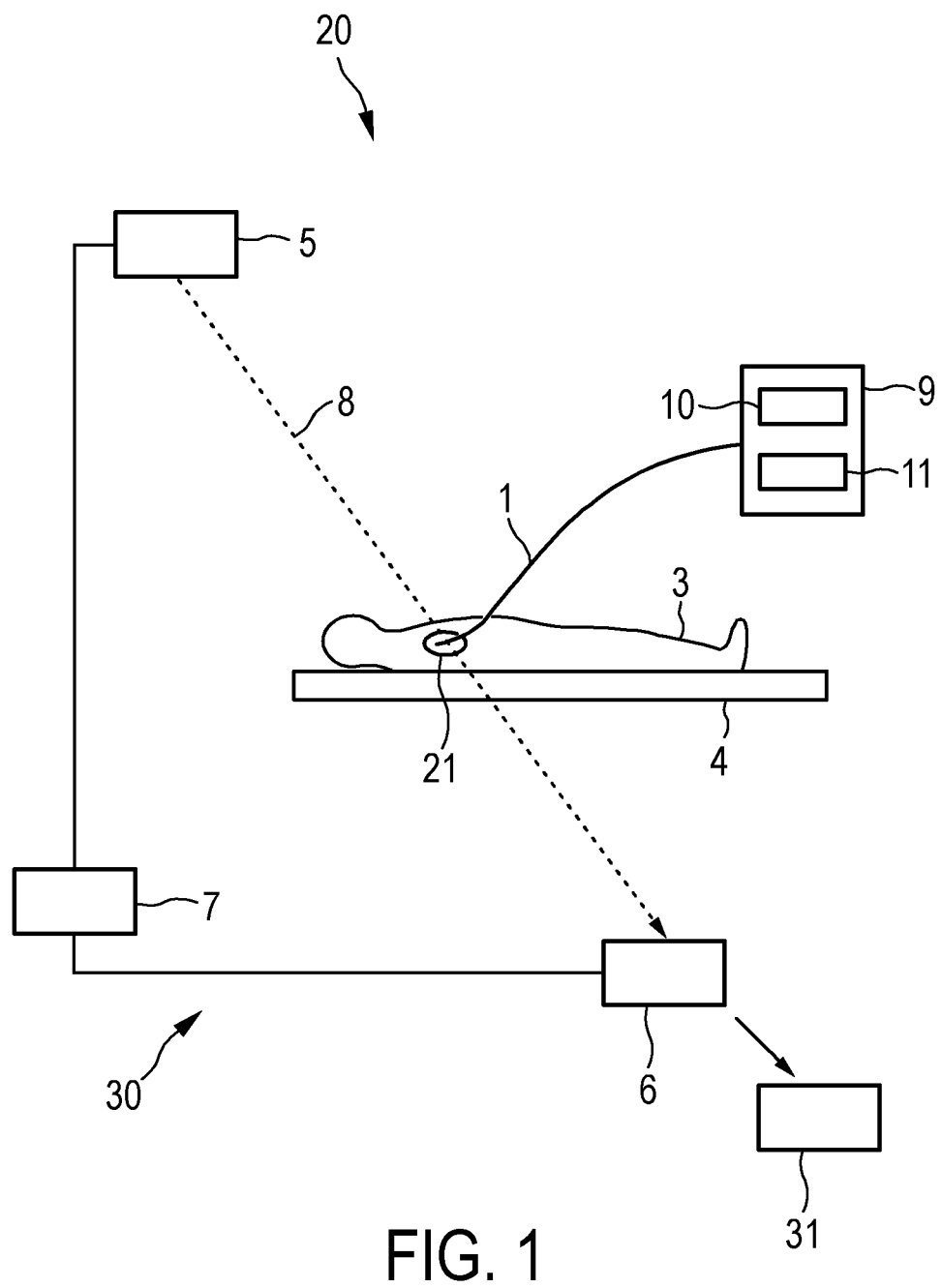
FIG. 1 shows schematically and exemplarily an embodiment of an interventional apparatus for performing an interventional procedure.

FIG. 1 shows schematically and exemplarily an embodiment of an interventional apparatus for performing an interventional procedure. In this embodiment the interventional apparatus is an ablation apparatus for performing an ablation procedure. However, in other embodiments the interventional apparatus can also be another apparatus being adapted to perform another interventional procedure.

The interventional apparatus 20 comprises a steerable introduction element 1 for being introduced into an object. In this embodiment the steerable introduction element 1 is an ablation catheter for being introduced into the heart 21 of a person 3 lying on a support element 4 like a patient table. The ablation catheter 1 preferentially comprises ablation electrodes at the tip of the ablation catheter 1 for ablating cardiac tissue at desired locations within the heart 21. The provision of the ablation energy can be controlled via an ablation energy control unit 11 of a control system 9. The ablation energy control unit 11 comprises an ablation power source for providing ablation power like radiofrequency power which can be supplied to the tip of the ablation catheter 1 by using electrical wires within the ablation catheter 1.

The ablation catheter 1 comprises a tube 2 made of a composite material including a shape memory alloy material and a non-memory polymer material. Generally, the non-shape-memory polymer material can be any polymer material, which is not a shape memory polymer material as described, for instance, in the above mentioned article. The tube 2 is schematically and exemplarily shown in more detail in FIG. 2.

Figure 2:
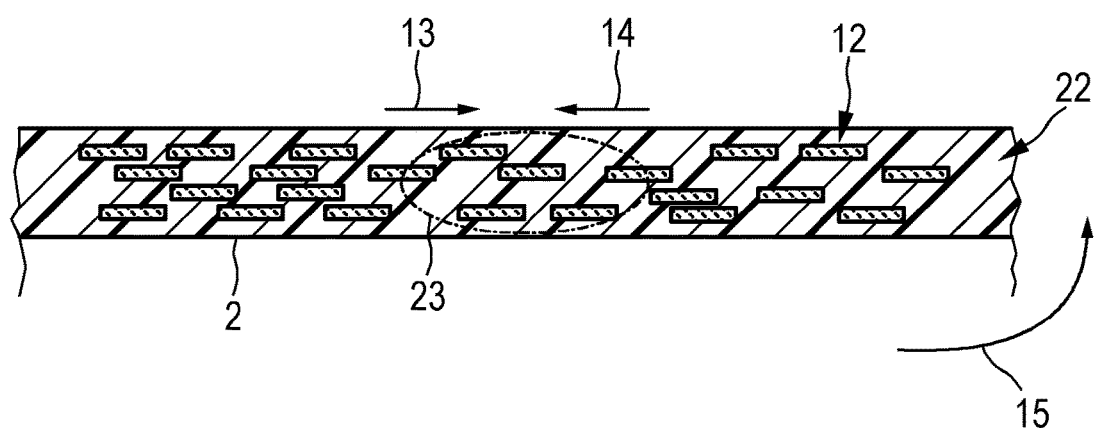
FIG. 2 shows schematically and exemplarily a tube of the interventional apparatus.

As can be seen in FIG. 2, the tube 2 comprises the non-shape-memory polymer material 22 and the shape memory alloy material 12, wherein in this embodiment the shape memory alloy material 12 is provided as fibers. The fibers can be, for instance, chopped fibers or wire pieces. The fibers 12 can increase the stiffness of the tube 2. The fibers 12 are made of nitinol. The surface of the fibers is preferentially roughened, for instance, forged, grinded, etched, blasted, et cetera, in order to increase the adhesion between the non-shape-memory polymer material and the shape memory alloy fibers.

The non-shape-memory polymer material 22 is preferentially at thermoplastic, silicone or thermoset. The non-shape-memory polymer material 22 can also be a combination of two of these materials or of all of these materials.

The tube 2 is producible by using a polymer shaping technique being preferentially a conventional one like extrusion or injection molding. In particular, if the tube is produced by using extrusion, the shape memory alloy fibers 12 will automatically be aligned in the length direction of the tube 2 within the non-shape-memory polymer material 22.

The composite material formed by the non-shape-memory polymer material 22 and the shape memory alloy fibers 12 can further comprise additives like additional conductive particles, which may be metal particles or carbon particles, in particular, carbon nanotubes, or ceramic particles. These additional particles can be used for modifying the thermal conductivity of the composite material. Moreover, these particles can be used for modifying the electrical resistance of the tube such that, for instance, a part of the tube 2 can be heated by resistive heating. These particles or other additional particles can also be used for increasing the stiffness of the tube 2.

The steerable introduction element 1 further comprises a temperature modifying element for modifying the temperature of a part of the tube 2 relative to another part of the tube 2 for bending the tube 2. By modifying the temperature of a part of the tube 2 the temperature of the tube 2 can be locally modified, i.e. heated or cooled, causing the tube 2 to bend. In this embodiment, the temperature modifying element is a heating element adapted to heat a wall of the tube 2 at one side, in order to cause the tube 2 to bend. For instance, the heating element can be adapted to heat the elliptical region 23 shown in FIG. 2, which may lead to shrinkage as indicated by the arrows 13, 14, wherein this shrinkage can lead to a bending of the tube 2 as indicated by the arrow 15.

The heating element can be controlled by a temperature modifying element control unit 10 of the control system 9, which can be adapted to allow a user to heat the tube 2 at a desired location with a desired intensity, in order to bend and, thus, steer the tube 2 in a desired direction.

The heating element can be adapted to heat the respective part of the tube 2 by at least one of resistive heating, fluidic heating and optical heating. For instance, the heating element can be adapted to apply an electrical current to the tube 2 such that the tube material itself can be resistively heated at the desired location. Or, the heating element can comprise a separate element being adapted to heat the respective part of the tube 2 by fluidic, especially liquid, or optical heating. For instance, the heating element can comprise an optical fiber or another optical means for providing light to be absorbed by the part of the tube 2 to be heated.

The heating element can comprise several sub heating elements located at different locations for modifying the temperature of different parts of the tube 2, wherein at least two of the heating sub elements are controllable separately from each other. By addressing different heating sub elements different bendings of the tube 2 can be obtained for steering the introduction element 1 as desired. The heating sub elements can be adapted and controlled such that the tube 2 can be bent in different directions, in particular, in all directions, preferentially at any location along the tube length.

The temperature modifying element can also comprise a cooling element being adapted to provide a fluidic cooling for cooling a part of the tube 2 for bending the same. The cooling element can be used to reset the steerable introduction element faster into its original position, after a thermal activation by heating has been stopped. Alternatively or in addition, after a certain part of the tube has been thermally activitated by heating the same and after this heating has been stopped, an opposite part of the tube can be heated for resetting the tube and, thus, the steerable introduction element faster into its original position.

In the following several arrangements of heating elements and cooling elements for heating and cooling, respectively, the tube will exemplarily be described with reference to FIGS. 3 to 7.

Figure 3:
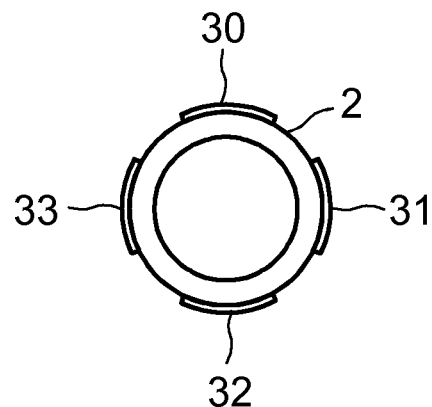
FIG. 3 shows schematically and exemplarily a tube with several temperature modifying sub elements.

FIG. 3 shows schematically and exemplarily four heating elements 30 . . . 33 equidistantly arranged along the circumference of the tube 2. Each heating element 30 . . . 33 can be separately electrically connected to the temperature modifying element control unit 10, which in this example may be an electrical current source, in order to apply electrical current to the several heating elements 30 . . . 33 independently from each other. Preferentially, at several longitudinal positions along the length direction of the tube 2 different sets of heating elements 30 . . . 33 are arranged, in order to allow the tube 2 to be bent at different longitudinal positions along the length direction. The heating elements can also be arranged only at the inner circumference of the tube 2 or the heating elements can be arranged on the outer circumference and on the inner circumference of the tube 2.

Figure 4:
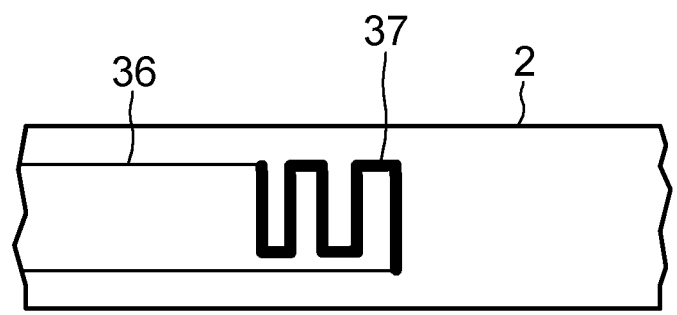
FIG. 4 shows schematically and exemplarily a resistive heating element arranged on a tube.

FIG. 4 shows schematically and exemplarily a resistive heating element 37 arranged on the tube 2. The resistive heating element 37 is electrically connected to the temperature modifying element control unit 10 via electrical conductors 36 like electrical wires. Also in this embodiment the temperature modifying element control unit 10 is a current source for applying electrical current to the resistive heating element 37. Although in FIG. 4 only a single resistive heating element 37 is shown for illustrative purposes, also more resistive heating elements can be arranged on the tube 2 for heating the tube 2 at the respective locations.

Figure 5:
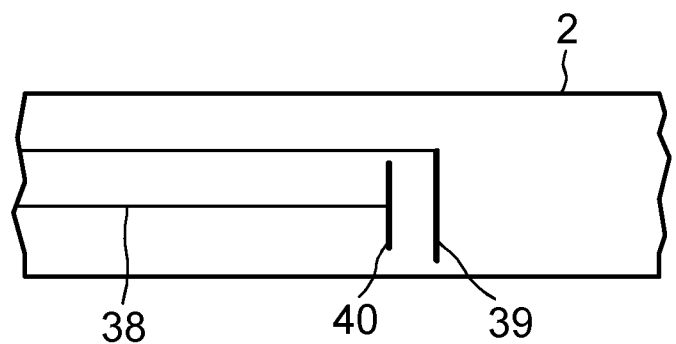
FIG. 5 shows schematically and exemplarily electrical connections arranged on a tube for applying electrical current to the tube.

FIG. 5 shows schematically and exemplarily a further possible heating element. In this example the heating element comprises electrical connections 38, 39, 40 for introducing electrical current into the tube 2, wherein in this embodiment the tube 2 itself can generate heat by resistive heating. Thus, the electrical connections 38, 39, 40 are substantially only used for applying electrical current to the tube 2, wherein the heat is substantially generated in the composite material of the tube 2. Also in this embodiment the temperature modifying element control unit 10 is preferentially a current source for providing the electrical current to be applied to the tube 2. The electrical connections 38 are preferentially insulated.

The heating elements, for instance, the heating elements 30 . . . 33 and the resistive heating element 37, can be separate components. For instance, they can be formed by a resistive pattern on a foil, wires or a dispensed pattern on the tube. The electrical connections like the electrical connections 36, 38, 39, 40 can be wires, dispensed lines, conducting lines on a flex foil, et cetera.

Figure 6:
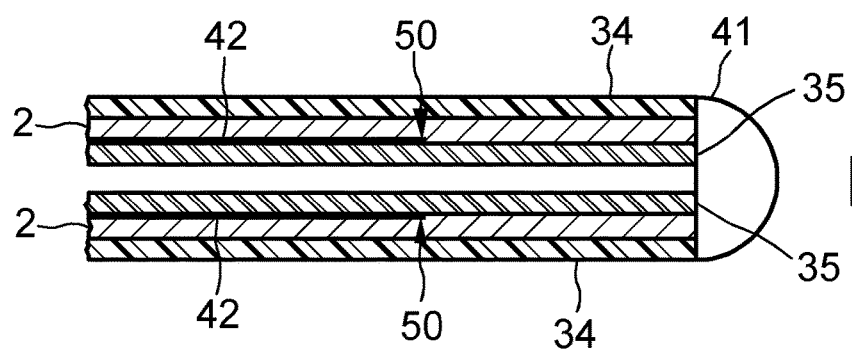
FIG. 6 shows schematically and exemplarily a tip of an introduction element comprising an optical heating element.

FIG. 6 shows schematically and exemplarily a further possible arrangement for heating the tube 2. In this embodiment the steerable introduction element is an ablation catheter having an ablation electrode 41, an inner tube 35 and an outer tube 34. In between the inner tube 35 and the outer tube 34 the tube 2 being an intermediate tube and having the composite material including the shape memory alloy material and the non-shape-memory polymer material is arranged. Optical fibers 42 are located adjacent to the intermediate tube 2, in order to optically heat the intermediate tube 2. The intermediate tube 2 is optically heated at the ends 50 of the optical fibers 42. In this embodiment the temperature modifying element control unit 10 comprises a light source for providing light to be coupled into the optical fibers 42 for optically heating the intermediate tube 2. In FIG. 6, the optical fibers 42 are arranged between the inner tube 35 and the intermediate tube 2. However, alternatively or in addition, optical fibers 42 can also be arranged between the intermediate tube 2 and the outer tube 34. Electrical connections for connecting the ablation electrode 41 to the ablation energy control unit 11 are not shown in FIG. 6 for clarity reasons.

The introduction element, in particular, the ablation catheter, can comprise an active cooling as it is known from known ablation catheters. This known active cooling can also be used to actively cool the tube 2, in particular, the composite material including the shape memory alloy material and the non-shape-memory polymer material. Using active cooling can make the steering faster. However, the introduction element may also not comprise a separate cooling element and just provide a natural cooling using, for instance, metal components like a braiding, a coil, et cetera, which may be used for providing desired mechanical properties.

Figure 7:
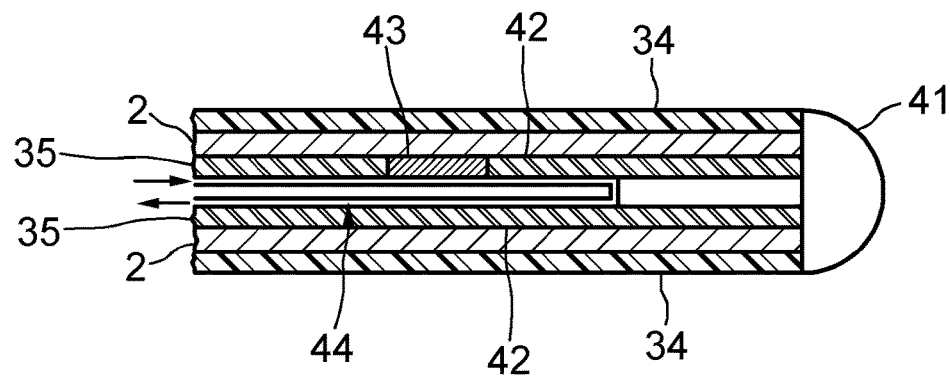
FIG. 7 shows schematically and exemplarily a tip of an introduction element comprising a fluidic heating and cooling element.

FIG. 7 shows schematically and exemplarily an embodiment of the introduction element providing an active fluidic cooling and an active fluidic heating. Also in this embodiment the introduction element comprises an outer tube 34, an inner tube 35 and an intermediate tube 2 arranged in between the outer tube 34 and the inner tube 35. Optical fibers 42 are located between the inner tube 35 and the intermediate tube 2. The intermediate tube 2 comprises the composite material including the shape memory alloy material and the non-shape-memory polymer material. Within the inner tube 35 a channel 44 is provided for allowing fluid to flow from a fluid source to a conductive element 43 and from the conductive element 43 back to the fluid source. The conductive element is a part of the inner tube 35 and forms a kind of bridge for allowing the temperature of the provided fluid to be transferred to the intermediate tube 2. The conductive element 43 is preferentially a metal segment introduced into the inner tube 35 for heat exchange. The channel 44 can be provided by using extra tubing or a lumen as generally present in ablation catheters. By providing a relatively cold fluid the intermediate tube 2 can be cooled down and by providing a relatively hot fluid the intermediate tube 2 can be heated. In this embodiment the fluid source is preferentially part of the temperature modifying element control unit 10 for allowing the temperature modifying element control unit 10 to control the temperature of the intermediate tube 2 by providing the fluid with a desired temperature. Also in this embodiment the ablation electrode 41 is electrically connected to the ablation energy control unit 11 via electrical connections like electrical wires not shown in FIG. 7 for clarity reasons.

A position detection apparatus 30 is used for detecting the position of the tip of the catheter 1 within the person 3. In this embodiment the position detection apparatus 30 comprises an x-ray source 5 for providing x-rays 8 traversing the person 3 and being detected by an x-ray detector 6, after having traversed the person 3. The x-ray source 5 and the x-ray detector 6 are controlled by a position detection control unit 7.

The position detection apparatus 30 is adapted to generate x-ray projection images of the inside of the person 3 including the catheter 1, in particular, including the tip of the catheter 1. The projection images can be shown on a display 31 to a user such that the user can steer the catheter 1 within the person 3 depending on the projection images shown on the display 31.

Figure 8:
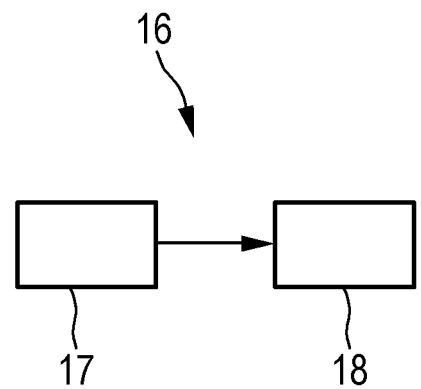
FIG. 8 shows schematically and exemplarily a production apparatus for producing the tube of the interventional apparatus.
Figure 9:
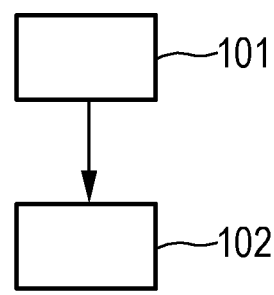
FIG. 9 shows a flowchart exemplarily illustrating an embodiment of a production method for producing the tube of the interventional apparatus.

FIG. 8 shows schematically and exemplarily a production apparatus 16 for producing the tube 2 and FIG. 9 shows a flowchart exemplarily illustrating an embodiment of a production method for producing the tube 2 by using the production apparatus 16 shown in FIG. 8.

The production apparatus 16 comprises a composite material providing unit 17 for providing a composite material comprising shape memory alloy material and non-shape-memory polymer material. This provision of the composite material is performed in step 101. In this embodiment a composite material is provided comprising shape memory alloy fibers like nitinol fibers and a non-shape-memory polymer material like thermoplastic, silicone and/or thermoset. The shape memory alloy fibers can be made from a wire that is chopped into wire parts forming the fibers. These wire parts can be mixed with the non-shape-memory polymer material using polymer mixing equipment like a mixer, a kneader, a twin screw extruder, et cetera.

The production apparatus 16 further comprises a polymer shaping unit 18 for producing the tube 2 by applying a polymer shaping technique to the provided composite material. This application of the polymer shaping technique is performed in step 102. In this embodiment the polymer shaping unit 18 uses extrusion for producing the tube 2.

Although in the above described embodiment the introduction element is an ablation catheter, in other embodiments the introduction element can also be another one. For instance, it can be another kind of catheter, an endoscope or a sheath. The tube, in particular, the introduction element comprising the tube, is preferentially adapted for minimal invasive surgery.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the control of the ablation energy provision or of the heating and/or cooling for bending the tube as desired performed by one or several units or devices can be performed by any other number of units or devices.

Any reference signs in the claims should not be construed as limiting the scope.

The invention claimed is:

1. A steerable introduction element for being introduced into an object, the steerable introduction element comprising:
   a first tube;
   a second tube having a thermally conductive element,
   an intermediate tube arranged in between the first tube and the second tube, the intermediate tube being producible by applying a polymer-shaping technique to a composite material that includes pieces of a shape memory alloy material embedded in a non-shape-memory polymer material; and
   a temperature modifying element for modifying the temperature of at least a part of the intermediate tube for bending the intermediate tube,
   wherein the thermally conductive element is configured to transfer heat between the second tube and the intermediate tube, and
   wherein at least two of the pieces of the shape memory alloy material are separated from each other along a longitudinal direction of the intermediate tube by the non-shape-memory polymer material and a first piece of the at least two of the pieces overlaps with a second piece of the shape memory alloy material along a perpendicular direction perpendicular to the longitudinal direction of the intermediate tube, the first piece being adjacent to the second piece in the perpendicular direction and extending beyond the second piece along the longitudinal direction.

2. The steerable introduction element as defined in claim 1, wherein the temperature modifying element comprises at least one of a heating element and a cooling element.

3. The steerable introduction element as defined in claim 2, wherein the heating element is adapted to heat the part of the tube by at least one of resistive heating, fluidic heating and optical heating.

4. The steerable introduction element as defined in claim 1, wherein the temperature modifying element comprises several temperature modifying sub elements located at different locations for modifying the temperature of different parts of the tube, wherein at least two of the temperature modifying sub elements are separately controllable.

5. The steerable introduction element as defined in claim 1, wherein the steerable introduction element is a steerable sheath, a steerable catheter or a steerable endoscope.

6. The steerable introduction element of claim 1, wherein the second tube defines a channel configured to receive a fluid having a predetermined temperature for one of heating and cooling the intermediate tube.

7. The steerable introduction element of claim 1, further comprising a resistive heating element located on the intermediate tube.

8. The steerable introduction element of claim 1, further comprising electrical connections configured to introduce electrical current into the intermediate tube.

9. The steerable introduction element of claim 1, wherein the pieces of the shape memory alloy material comprises individual elongated shape memory alloy elements, and wherein a surface of the individual elongated shape memory alloy elements is surface treated such that adhesion between the individual elongated shape memory alloy elements and the non-shape-memory polymer material is increased.

10. The steerable introduction element of claim 1, wherein the composite material further comprises at least one of a metal material, a carbon material and a ceramic material configured to modify at least one of thermal conductivity, electrical resistance and stiffness of the intermediate tube.

* * * * *